United States Patent [19]

Murao et al.

[11] Patent Number: 5,372,816
[45] Date of Patent: Dec. 13, 1994

[54] TREHALOSTATIN AND PROCESS FOR THE PREPARATION THEREOF

[75] Inventors: Sawao Murao, Sakai; Takashi Shin, Sanda, both of Japan

[73] Assignee: Suntory Limited, Osaka, Japan

[21] Appl. No.: 948,236

[22] Filed: Sep. 21, 1992

Related U.S. Application Data

[62] Division of Ser. No. 601,738, Dec. 6, 1990, Pat. No. 5,169,778.

[30] Foreign Application Priority Data

Feb. 28, 1989 [JP] Japan .................. 64-45394

[51] Int. Cl.$^5$ .............. A01N 63/00; C12P 7/00; C12N 1/20; C07H 5/04
[52] U.S. Cl. .................. 424/405; 424/93.4; 435/100; 435/132; 435/155; 435/169; 435/252.1; 435/822; 435/911; 536/18.7
[58] Field of Search .......... 536/18.7; 435/100, 132, 435/155, 169, 252.1, 822, 911; 424/93 D, 405

[56] References Cited

U.S. PATENT DOCUMENTS

4,920,215  4/1990  Holdom et al. ............ 536/16.8
4,981,799  1/1991  Takahashi et al. ......... 435/233
5,169,778 12/1992  Marao et al. ............. 424/93 D

FOREIGN PATENT DOCUMENTS

1544068  4/1977  United Kingdom ........... 407/14

OTHER PUBLICATIONS

The Journal of Antibiotics, vol. 41, No. 10, pp. 1506–1510 (1988).
The Journal of Antibiotics, vol. 41, No. 11, pp. 1525–1532 (1988).
Biochemical and Biophysical Research Communications, vol. 77, No. 2, pp. 449–456 (1977).
Chemical Abstracts, vol. 111, No. 21, p. 331, ab. No. 190010 j (1989).
The Journal of Antibiotics, vol. XI, No. 4, pp. 563–565 (1987).
Sneath et al., Bergey's Manual, Systematic Bacteriology, vol. 2, pp. 1465, 1469, 1470, 1495 and 1500.
Gherna et al., ATCC, Catalogue of Bacteria and Pha-es, 17th ed., p. 16 (1989).

*Primary Examiner*—David M. Naff
*Assistant Examiner*—Deborah K. Ware
*Attorney, Agent, or Firm*—David G. Conlin; Ernest V. Linek

[57] ABSTRACT

This invention relates to the substance Trehalostatin which is a white powder soluble in water but hardly or only slightly soluble in hexane, benzene, ethers and petroleum ether, shows no absorption maxima at 220 nm or above in its ultraviolet visible light absorption spectrum, is positive in Rydon-Smith reaction and negative in nynhydrin reaction, 3,6-dinitrophthalic acid reaction and Elson-Morgan reaction, and has an RF value of 0.37 in Merck Kieselgal 50 $F_{254}$ thin-layer chromatography using 3:1:2 mixture on n-butanol, acetic acid and water as a developing solvent, Rt of 11.0 minutes in YMC PA03 (0.7 ×27 cm) high performance liquid chromatography using 65% v/v acetonitrile (in $H_2O$) as a solvent at a flow rate of 1.0 ml/min, a molecular weight of 366, [alpha]$_D$ of +115°, and specific NMR spectrum.

Also disclosed is a process for preparing trehalostatin and a specific strain of *Amycolatopsis trehalostatica* which has FERM accession number BP-2784.

In addition the trehalostatin compound shows an inhibitory effect against trehalase in insects, especially *Aldrichina grahami*, even at a very low concentration and is therefore useful as an insecticide.

3 Claims, No Drawings

TREHALOSTATIN AND PROCESS FOR THE PREPARATION THEREOF

CROSS-REFERENCE TO RELATED APPLICATION

This is a divisional of co-pending application Ser. No. 07/601,738 filed on Dec. 6, 1990 now U.S. Pat. No. 5,169,778.

TECHNICAL FIELD

The present invention relates to the substance Trehalostatin. The invention also relates to a process for the preparation of said substance Trehalostatin and *actinomycetes* which produce said substance.

BACKGROUND ART

Trehalase is one of the glucohydrolases. It is an enzyme which catalyzes hydrolysis of the alpha-glucosidic linkage of trehalase which is widely distributed in mold, yeast and hemolymph of many species of insects.

SUMMARY OF THE INVENTION

The present inventors found that the *actinomycetes* belonging to the genus Amycolatopsis, which had been separated from soil, can yield a substance which shows an inhibitory effect against trehalase in insects, especially in *Aldrichina grahami*, at a very low concentration. This substance was named Trehalostatin.

The present invention was accomplished on the basis of said finding, and it relates to the substance Trehalostatin which has been collected from the cultures of a trehalostatin-producing *actinomycete* belonging to the genus Amycolatopsis. The present invention also provides *actinomycetes* strains which can yield such a substance and a process for the preparation of Trehalostatin by using said strains.

*Amycolatopsis trehalostatics* SAM 0967 has the following taxonomical properties.

1. Morphological characteristics

The substrate and aerial mycelium are formed and measure 0.4–0.8 μm in diameter. The substrate mycelium is branched and exhibits occasional fragmentation. The aerial mycelium is also branched and formed spore chain with 10 or more spore per chain. Each spore measures 0.4 to 0.5 μm in width and 0.9 to 1.3 μm in length and has a smooth surface. No sporangia, synnemata, or sclerotia were observed even after 21 days of cultivation.

2. Cultural characteristics

Sucrose-nitrate agar: aerial mycelium are abundant and white; brownish orange in reverse; soluble pigment is grayish purple.

Glucose-asparagine agar: aerial mycelium are abundant and white; grayish orange in reverse; no soluble pigment.

Glycerol-asparagine agar: aerial mycelium are abundant and white; grayish brown in reverse; soluble pigment is grayish orange.

Starch-inorganic acid agar: aerial mycelium are abundant and white; whitish yellow in reverse; no soluble pigment.

Tyrosine agar: aerial mycelium are abundant and white; dark brown in reverse; soluble pigment is grayish brown.

Nutrient agar; aerial mycelium are abundant and white; whitish yellow in reverse; no soluble pigment.

Yeast extract-malt extract agar: aerial mycelium are abundant and white; dark brown in reverse; soluble pigment is grayish brown.

Oatmeal agar: aerial mycelium are abundant and white; whitish yellow in reverse; no soluble pigment.

1/10 potato-carrot agar: aerial mycelium are abundant and white; whitish yellow in reverse; no soluble pigment.

1/10 V-8 juice agar: aerial mycelium are abundant and white; whitish yellow in reverse; no soluble pigment.

3. Physiological characteristics (1) Growth temperature

As a result of culture tests conducted at temperature of 16° C., 19° C., 22° C., 25.5° C., 28.5° C., 31° C., 33° C., 36.5° C., 39.5° C., 42.5° C., 45.5° C. and 47° C. by using Yeast extract-glucose broth, the temperature range for growth was 19°–39.5° C., with optimum growth occurring at 28.5°–36.4° C.

(2) Gelatin liquefaction (28°)
Glucose-peptone-gelatin medium: positive
Simple gelatin medium: positive
Meat extract-gelatin medium: positive
(3) Hydrolysis of starch: positive
(4) Coagulation of skim milk (28° C.): negative
(5) Peptonization of skim milk: positive
(6) Formation of melanin-like pigment
Peptone-yeast extract iron agar: negative
Tyrosine agar: negative
Triptone-yeast extract agar: negative
(7) Reduction of nitrate: positive
(8) Utilization of carbohydrates (tested on Pridham and Gottlieb carbon utilization medium at 28° C. for 14 days)

| | |
|---|---|
| D-glucose: | + |
| D-xylose: | + |
| L-lactose: | + |
| L-rhamnose: | + |
| L-arabinose: | + |
| D-fructose: | + |
| Raffinose: | ± |
| D-mannitol: | + |
| Inositol: | + |
| Sucrose: | + |
| Lactose: | + |

(notes)
+: utilized; ±: doubtful; −: not utilized (9) Acid production from carbohydrates

| | |
|---|---|
| Raffinose: | + |
| Inositol: | + |
| Lactose: | + |
| Sorbitol: | − |
| Erythritol: | − |
| L-arabinose: | + |
| Adonitol: | − |
| D-galactose: | + |

As determined by the method described by R. E. Gordon et al., *International Journal of Systematic Bacteriology*, vol. 24, p. 54, 1974.

4. Chemotaxonomy (1) 2,6-diaminopimelic acid

The presence of meso-2,6,-diaminopimelic acid was detected as a result of examination of the hydrolyzate of the whole cell and its cell wall according to the method described by J. L. Staneck and G. D. Roberts, *Applied Microbiology*, vol. 28, p. 226, 1974.

(2) Sugars

The presence of arabinose was detected in the hydrolyzate of the whole cell. There was also discovered the presence of galactose and arabinose in the hydrolyzate of the cell wall.

(3) Menaquinones

MK-9 (H4) is the major menaquinone component.

(4) Phospholipid type

The present actinomycete strain contains phosphatidyl ethanolamine and does not contain phosphatidyl choline and an unknown glycosamine-containing phospholipid. This falls under type P II phospholipid pattern according to M. P. Lechevalier and H. A. Lechevalier, "The Chemotaxonomy of Actinomycetes," pp. 227–291, in *Actinomycete Taxonomy*, Special Publication No. 6, Society for Industrial Microbiology (edited by A. Dietz and D. W. Thayer), U.S.A., 1980.

(5) Mycolic acid

No mycolic acid was detected in the cell.

The SAM 0967 strain has a type IV cell wall composition (meso-2,6-diaminopimelic acid, galactose and arabinose as diagnostic constituents) and a type A whole-cell sugar pattern (arabinose and galactose). The SAM 0967 strain produces an aerial mycelium forming spore chain with 10 or more smooth-surfaced spores per chain at the end of each aerial mycelium. The major menaquinone component of the SAM 0967 strain is of then MK-9 (H4). Its phospholipid type is P-II. No mycolic acid is detected.

From the above described taxonomical properties, the SAM 0967 strain can be identified as an actinomycete belonging to the genus Amycolatopsis. At present, 6 species and 1 subspecies are assigned to the genus Amycolatopsis.

Referring to M. P. Lechevalier et al., *International Journal of Systematic Bacteriology*, vol. 36, p. 29, 1986, and A. Henssen et al., *International Journal of Systematic Bacteriology*, vol. 37, p. 292, 1987, SAM 0967 is found to resemble *Amycolatopsis orientalis* and *Amycolatopsis mediterranei*. The present inventors made a comparison of taxonomic properties between SAM 967 strain and the type strains of *Amycolatopsis orientalis* and *Amycolatopsis mediterranei*.

As seen in the table which follows, the SAM 0967 strain is clearly distinguished from *Amycolatopsis orientalis* by the color of aerial mycelium on Yeast extract malt extract agar and inorganic salts-starch agar, growth in the presence of 5% NaCl, utilization of sucrose, acid production from raffinose, erythritol and adonitol, and menaquinone composition.

Also the SAM 0967 strain is clearly distinguished from *Amycolatpsis mediterranei* by the formation of aerial mycelium and menaquinone composition.

The present inventors considered these differences to be sufficient to taxonomically distinguish SAM 0967 strain from said two species; thus the present inventors concluded that the SAM 0967 strain represents a new species within the genus Amycolatopsis. So the present inventors named SAM 967 strain *Amycolatopsis trehalostatica*.

*Amycolatopsis trehalostatica* SAM 0967 was deposited under FERM P-10544 at the Fermentation Research Institute of Agency of Industrial Science and Technology at the date of Feb. 17, 1989, and later it was converted, on Feb. 28, 1990, to an international deposit under the Budapest Treaty on the International Recognition of the Deposit of Microorganisms for the Purpose of Patent procedure and given FERM accession number BP-2784.

TABLE

Comparison of taxonomical properties of SAM 0967 strain with those of *Amycolatoposis orentalis* JCM-4600 and *Amycolatopsis mediterranei* JCM-4789

| Properties | SAM 0967 | A. orientalis JCM-4600 | A. mediterranei JCM-4789 |
|---|---|---|---|
| Aerial mycelium - forming ability | +++ | +++ | −* |
| Color tone of aerial mycelium | White | White (blue) | − |
| Growth in the presence of 5% NaCl | − | + | − |
| Utility of carbon sources | | | |
| Sucrose | + | − | + |
| Acid-forming ability | | | |
| Raffinose | + | − | + |
| Erythritol | − | + | − |
| Adonitol | − | + | − |
| Menaquinone composition** | | | |
| MK-9 | − | + | − |
| MK-9 (H2) | − | ++ | + |
| MK-9 (H4) | +++ | +++ | +++ |

(Notes)
*: No aerial mycelium was formed on a morphological observation plate, but white aerial mycelia were formed slightly on a carbon source utility plate.
**: The compositional ratio (%) of menaquinone contained was indicated according to the following 4-stage rating system: −: <5%; +: 5–14%; ++: 15–49%; +++: >50%

DETAILED DESCRIPTION OF THE INVENTION

The present inventors believe that the differences provided above are enough to taxonomically distinguish strain SAM 0967 from said two species; thus the present inventors have concluded that strain SAM 0967 represents a new species within the genus Amycolatopsis. Therefore, the present inventors have designated strain SAM 0967 as. *Amycolatopsis trehalostatica*.

*Amycolatopsis trehalostatica* SAM 0967 was deposited under accession number FERM P-10544 at the Fermentation Research Institute of Agency of Industrial Science and Technology at the date of Feb. 17, 1989, and later it was transferred, on Feb. 28, 1990, to international deposition made under the requirements of the Budapest Treaty on the International Recognition of the Deposit of Microorganisms for the Purpose of Patent procedure, from which it is available under accession number FERM BP-2784.

In the present invention, the actinomycetes such as those described above are cultured. A medium used for the cultivation may be either liquid or solid, but usually shaking culture or aerated spinner culture in a liquid medium is expedient.

It is possible to use any type of medium as far as it enables growth of the actinomycetes according to the present invention and is capable of accumulating the substance of this invention. As carbon source, for instance, there may be used glucose, lactose, starch, sucrose, dextrin, molasses, organic acids, etc. As nitrogen source, there may be used protein, hydrolyzates such as peptone and Casamino acid, meat extract, yeast extract, soybean cake, corn steep liquor, amino acids, ammonium salts, nitrates and other organic or inorganic nitrogen compounds. Various types of phosphates, magnesium sulfate, sodium chloride and the like may be added as an inorganic salt. Also, vitamins, nucleic acid-associated compounds and such may be added for the purpose of promoting growth of the actinomycete. In some cases, it is effective for promoting accumulation amount of the substance of this invention to add a defoaming agent such as silicon, polypropylene glycol derivatives, soybean oil and the like medium.

In carrying out the cultivation in the present invention, it is desirable to initially perform a small-scale pre-cultivation and to inoculate the resulting culture into a medium to conduct the primary cultivation. In both preliminary and primary cultivation, the culturing conditions such as cultivation temperature, cultivation period and properties of the culture medium are properly selected and adjusted so as to maximize the amount of the substance of this invention accumulated in the medium. In many cases, the cultivation is preferably carried out under an aerobic condition at a temperature of 25°–30° C. In case of using a liquid medium, it is recommended to maintain ph of the medium at 5.5–8.0. In the course of such cultivation, the substance of the present invention is produced and accumulated in the culture. When cultivation is carried out by using the liquid medium, the objective substance is accumulated principally in a liquid phase portion of the medium, so that it is desirable to filter or centrifuge the cultures to remove the cells and then to separate the objective substance from the filtrate or supernatant. In certain cases, however, the objective substance may be directly separated from the liquid culture without removing the cells from them.

The detection and determination of the substance Trehalostatin of this invention during the separation and collection can be accomplished by determining the degree to which said substance can inhibit an activity of trehalase extracted from *Aldrichina grahami* or porcine kidney. For the separation and purification of the objective substance from the cultures, there can be employed various means in accordance with chemical characteristics of the substance of this invention. For instance, it is effective to employ treatment with an organic solvent, gel filtration by Sephadex or Biogel, ion exchange chromatography using various types of ion exchange resin, adsorption chromatography using an absorbent such as activated carbon, silica gel and Amerlite XAD-1 or XAD-2 and normal-phase chromatography using a carrier such as YMC-PA 43 or TSK-Amide 80. By using these means in a proper combination, the substance Trehalostatin of this invention can be isolated as white amorphous powder. Other methods than those mentioned above may also be used as far as such methods can effectively utilize the characteristics of the substance of this invention. An especially preferred combination the absorbent is that of Dowex 50WX4 (H), YMC-PA43 and TSK-Amide 80.

The substance of this invention can be used after its isolation and purification, but in some cases, the culture of the Trehalostatin-producing actinomycete can be used in the form as it is or only after a simple purification.

EXAMPLES

The present invention will be described in detail below by showing the examples thereof, but the present invention is not limited to these examples.

EXAMPLE 1

Preparation of Trehalostatin (1) Activity determination method

The inhibitory activity of Trehalostatin in each stage of its purification was determined in the following way.

10 μl of an inhibitor solution and 10 μl of a trehalase solution (trehalase collected from *Aldrichina grahami*) were mixed. After 5 minutes incubation at 37° C., 80 μl of a 5 mM trehalose and 50 mM phosphate buffer solution (pH 6.5) was added, followed by an additional one-hour incubation at 37° C. Thereafter, 10 μl of a 50% trichloroacetic acid solution was added to terminate the reaction. Glucose formed in the reaction solution was determined by a new blood sugar test manufactured by Boehringer-Mannheim Ltd. The amount of the enzyme was such that absorbance of the wavelength (660 mm) used in the glucose determination when conducted according to the above method without adding the inhibitor would become 1.0. The Trehalostatin concentration which can achieve 50% inhibition of enzyme (trehalase) activity in the above determination method was expressed as 1 unit/ml.

(2) Preparation of Trehalostatin by cultivation of *Amycolatopsis trehalotatica*

30 ml of pure culture of SAM 0967 strain was inoculated into 3.1 liters of a medium (pH 7.0) composed of hot water extract of potato, glucose, dry yeast extract, potassium monophosphate and magnesium sulfate and cultivated in a 5-liter jar fermenter at 28° C. × for 120 hours (aeration, 1vvm; agitation, 400 rpm).

To 3.07 liters of supernatant (containing 101,000 unites of Trehalostatin) obtained by centrifugation of the culture, formic acid was added to a final concentration of 0.02 M. After adjusting pH of the solution to 3.1 with hydrochloric acid, the solution was applied to a column (6×37 cm) of Dowex 50W×4 (H) (mfd. by Muromachi Chemical Co., Ltd.). This column was washed with 3.0 liters of 0.2 M pyridine-formic acid buffer (pH 3.2) and the substance having the activity inhibiting trehalase of *Aldrichina grahami* was eluted in 3.5 liters of 0.4 M pyridine-acetic acid buffer (pH 4.2).

The active fraction (containing 120,000 units of Trehalostatin) was concentrated and evaporated to dryness under reduced pressure, and the residue was dissolved in a small quantity of water and pH of the solution was adjusted to 3.1 with hydrochloric acid. The insolubles in the solution was removed by centrifuge, and the resultant supernatant was passed through a column (3×12 cm) of Dowex 50W×4 (H). This column was washed with 0.5 liter of deionized water and then further washed with 3 liters of 0.2 M pyridine-formic acid buffer (pH 3.2) containing 30% (V/V) of methanol to elute the objective substance.

The fraction of the objective substance (containing 120,000 units of Trehalostatin) was concentrated under reduced pressure. The residue was uniformly suspended in 50% (V/V) acetonitrile and charged into a packed column for high-performance liquid chromatography (YMC-PA 43, 2.5×27 cm). This column was washed with a 65% (V/V) acetonitrile solution of a determined composition (flow rate: 5 ml/min.), and the eluate was fractionated in portions of 5.0 ml and detected by a differential refractometer. As a result, the fraction having trehalase-inhibiting activity (containing 119,000 units of Trehalostatin) was eluted at around 200 ml after the charging.

The fraction containing the objective substance was concentrated, dissolved in 40% (V/V) acetonitrile and charged into a packed column for high-performance liquid chromatography (TSK-Amide 80, 0.7×27 cm). This column was washed with a solvent of the same composition (flow rate: 1 ml/min.) and the eluate was fractionated in portions of 0.5 ml and detected by a differential refractometer. The fraction having trehalase-inhibiting activity was eluted at around 25–30 ml after the charging. The fraction of the objective substance (containing 118,000 units of Trehalostatin) was evaporated to dryness, added with water and then freeze-dried, thereby obtaining 1 mg of a pure objective substance.

EXAMPLE 2

Physiochemical Properties Of Trehalostatin

The substance separated from the culture of *Amycolatopsis trehalostatica* (SAM 0967) and purified according to Example 1 was named Trehalostatin.

The physical and chemical properties of this Trehalostatin are shown below:

Appearance: white powder.

Solubility: soluble in water but hardly or only slightly soluble in hexane, benzene, ethers and petroleum ether.

Ultraviolet and visible light absorption spectrum: having no absorption maxima at 220 nm or above.

Color reaction: positive in Rydon-Smith reaction and negative in ninhydrin reaction, 3,6-dinitrophthalic acid reaction and Elson-Morgan reaction.

Thin-layer chromatoraphy: Rf=0.37 (Merck Kieselgel 60 F254, developing solvent: 3:1:2 mixture of n-butanol, acetic acid and water).

High-performance liquid chromatography: Rt=11.0 min. (column: YMC PA03, 0.7×27 cm; solvent: 65% V/V acetonitrile in H$_2$O; flow rate: 1.0 ml/min.; detection: deferential refractometer).

Molecular weight: 366 (m/z 367, M+H, SIMS).

[alpha]$_D$: +115°.

$^1$M-NMR/D$_2$O: 3.3 (ppm), dd, 1 H; 3.5 (ppm), m, 1 H; 3.5 (ppm), t, 1 H; 3.6 (ppm), d, 1 H; 3.6 (ppm), dd, 1 H; 3.7 (ppm), d, 1 H; 3.7 (ppm), dd, 1 H; 3.8 (ppm), ddd, 1 H; 4.1 (ppm), dd, 1 H; 4.2 (ppm), d, 1 H; 4.8 (ppm), ddd, 1 H; 5.2 (ppm), d, 1 H.

$^{13}$C-NMR/D$_2$O: 63.5 (ppm); 64.8 (ppm); 72.4 (ppm); 72.8 (ppm); 74.8 (ppm); 75.8 (ppm); 76.2 (ppm); 83.0 (ppm); 83.2 (ppm); 83.4 (ppm); 85.6 (ppm); 89.9 (ppm); 163.8 (ppm).

A structural formula of the present substance that can be assumed from the above results in such as shown below as Formula 1 or Formula 2:

Formula 1

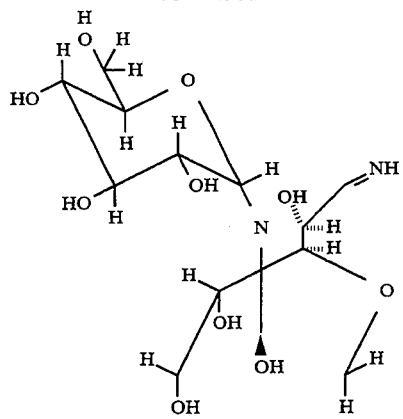

Formula 2:

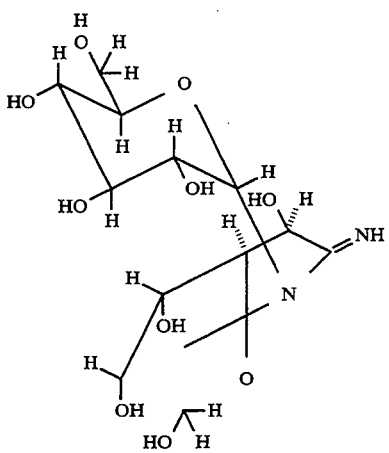

As shown below, the proposed Formula 1 and Formula 2 (supra) are not correct, and the correct structure of trehalostatin has been confirmed as being Formula 3:

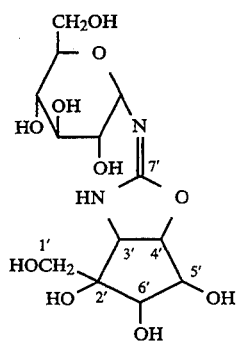

FORMULA 3

The confirmation of the assignment of Formula 3 to trehalostatin was made as follows. Trehalostatin is positive to chlorine - tolidine and vanillin-sulfate reagents, while negative to ninhydrin, 2,3,5-triphenyltetrazolium chloride, Elson-Morgan, and Tollens reagents.

These results confirm that Formula 3 should contain a saccharide moiety and a C—N linkage, but neither a reducing terminal nor a free amino group. A characteristic absorption band at 1610 cm$^{-1}$ among typical saccharide adsorption in its IR spectrum (film), as well as a UV end-absorption (in H₂O) suggested that Formula 3 was a saccharide with either amide or ureido functions.

The liquid SI-MS (secondary ion mass spectrometry), spectrum of Formula 3 furnished the [M+H]+ species at m/z 367, indicating a molecular formula of $C_{13}H_{22}O_{10}N_2$. A B/E linked scan on this molecular ion species yielded a daughter ion at m/z 205 [M+H—$C_6H_{10}O_5$]+, thus the presence of a hexose moiety was indicated and therefore the non-hexose moiety was $C_{13}H_{11}O_5N_2$ with 3 degrees of unsaturation.

A $^{13}$C—NMR (nuclear magnetic resonance) study of Formula 3 revealed the presence of a carbonyl carbon or equivalent at 163.8 ppm (in D₂O), indicating that the non-hexose moiety was bicyclic. Acetylation of Formula 3 with Ac₂O/pyridine at room temperature yielded 2 isomeric acetates, Formulas 4 and 4' in ca. 1:1 ratio. These are the positional isomers regarding N-acetates derived from two possible mutomers at the isoureido group.

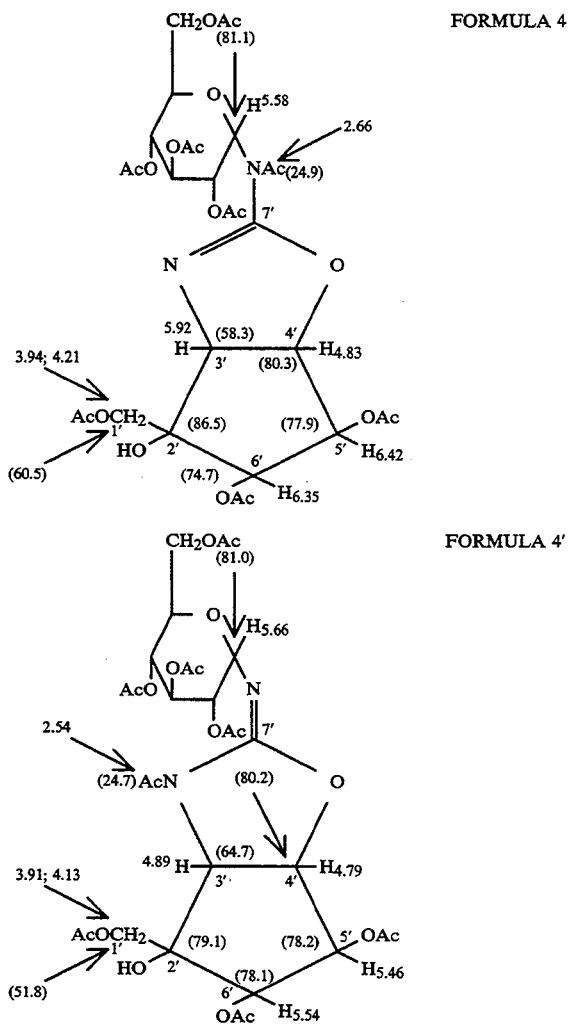

FORMULA 4

FORMULA 4'

Intensive NMR studies (500 MHz in CDCl₃) of the acetates (Formulas 4 and 4') allowed the present inventors to obtain the structure of Formula 3 as follows:

H,H-COSY (H,H-homonuclear shift correlation spectroscopy) experiments disclosed three isolated proton spins systems in the acetates as well as in Formula 3 itself, one being of an alpha-glucopyranosyl residue, and the rest, fragments 1 and II (FIG. 5).

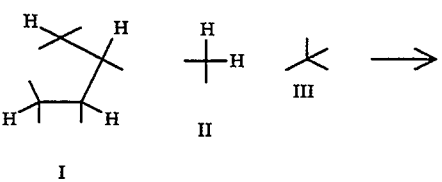

Figure 5

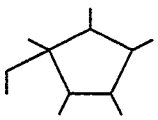

NOTE: In the fragments depicted in this Figure, a black dot represents a heteroatom, a black square represents a carbon atom and an open dot represents a heteroatom or a carbon atom.

The chemical shift of the anomeric carbon of the alpha-glucopyranosyl residue appeared up-field [delta$_C$ 81.1 and 81.0, respectively, for Formulas 4 and 4'] than would be expected for an O-glucoside suggesting that the glucopyranosyl residue was connected to nitrogen. Down-field chemical shifts of three contiguous carbons (by HMQC, $^1$H-delected multiple quantum coherence spectrum) in fragment I [delta$_C$ 80.2 (C-4'), 78.2 (C-5') and 78.1 (C-6')] of (Formula 4') are good evidence for their involvement in a five-membered ring system.

The involvement of fragment III, an sp³ quaternary carbon [delta$_C$ 86.5 and 79.1 for Formula 4 and Formula 4', respectively] in the five-membered ring system was obtained because two terminal protons of fragment 1 gave cross peaks with fragment 111 carbon in the HMBC ($^1$H-detected multiple-bond heteronuclear multiple quantum coherence spectrum) experiment. Both protons of the isolated methylene (fragment II) also showed cross peaks with the same quaternary carbon of fragment III. Thus the connectivity of these fragments was obtained as substructure IV.

The up-field resonance of C-3' (delta$_C$ 58.3) of Formula 4 proved that C-3' bears nitrogen. Deuterium-induced differential isotope shifts (DIS) observed on C-3' (delta$_C$ 76.2, Table 1) of Formula 3 was evidence for the presence of an NH group on C-3'. The large down-field shift upon acetylation of 1'-11 [from delta$_H$ 3.6/3.7 Formula 3 to 3.94/4.21 Formula 4 and 3.91/4.13 Formula 4', 5'-H [delta$_H$ 4.1 to 5.42 and 5.46] and 6'-H [delta$_H$ 3.8 to 6.35 and 5.54], indicated that Formula 3 bears free hydroxyl groups at the C-1', C-5' and C-6' positions. This was in good agreement with the DIS experimental result obtained for Formula 3 as shown in Table 1.

On the other hand 4'-H, the proton attached to C-4' on which no DIS was observed (Table 1) showed no remarkable down-field shift upon acetylation. Therefore, the oxygen linked to C-4' [delta$_C$ 89.9 for Formula 3, 80.3 for Formula 4 and 80.2 for Formula 4' is involved in further linkage. The substructure IV was thus extended to the structure with a cyclic isoureido function which is connected to the alpha-glucopyranosyl residue, when the nature of the remaining sp² carbon was taken into consideration.

On the basis of these spectroscopic data, the structure of trehalostatin acetates were obtained as shown in structures Formula 4 and Formula 4'. By comparing the NMR data of Formula 3 with those of Formula 4 and Formula 4', the structure of trehalostatin itself was confirmed as Formula 3.

TABLE I $^1H$ and $^{13}C$ NMR data of trehalostatin

| Carbon Number | $^{13}C$ | | $^1H$ |
|---|---|---|---|
| 1 | 83.4 (CH)$^{b,c}$ | | 5.2 (d, J=5.0) |
| 2 | 72.8 (CH)$^b$ | | 3.6 (dd, J=5.0, 9.0) |
| 3 | 75.8 (CH)$^b$ | | 3.5 (t, J=9.0) |
| 4 | 72.4 (CH)$^b$ | | 3.3 (dd, J=9.0, 10.0) |
| 5 | 74.7 (CH) | | 3.5 (ddd, J=10.0, 5.2, 2.5) |
| 6 | 64.8 (CH$_2$)$^b$ | a | 3.6 (dd, J=5.2, 12.3) |
|   |   | b | 3.7 (dd, J=2.5, 12.3) |
| 1' | 63.5 (CH$_2$) | a | 3.6 (d, J=12.3) |
|   |   | b | 3.7 (d, J=12.3) |
| 2' | 85.6 (C)$^{b,c}$ | | |
| 3' | 76.2 (CH)$^b$ | | 4.2 (br d, J=8.6, 0.1–0.2) |
| 4' | 89.9 (CH) | | 4.8 (ddd, J=8.6, 2.7, 0.1) |
| 5' | 83.2 (CH)$_{b,c}$ | | 4.1 (dd, J=2.7, 4.8) |
| 6' | 83.0 (CH)$^b$ | | 3.8 (ddd, J=4.8, 0.1–0.2, 0.1) |
| 7' | 163.8 (C) | | |

$^a$Chemical shifts are referenced to external TSP at 25° C., pD 8.9 (pD value is not corrected for the deuterium effect).
$^b$Indicates the presence of DIS, Among them, $^c$ denotes small DIS.

EXAMPLE 3

Enzyme Inhibition Spectrum of Trehalostatin

| Enzyme | Origin | Amount of enzyme (μg) | Reacting conditions | Activity measuring method | Action |
|---|---|---|---|---|---|
| Trehalase | (Aldrichina grahami)$^{4)}$ | 24* | pH 5.5, 5 mM trehalase | A | ++ |
|  | (Chaetomium aureum)$^{4)}$ | 15 | pH 5.5, 5 mM trehalase | A | + |
|  | (bovine colonic mucosa)1) | 2500 | pH 5.5, 5 mM trehalase | A | + |
|  | (swine kidney)$^{2)}$ | 1.1* | pH 6.5, 5 mM trehalase | A | + |
| α-glycosidase | (yeast)$^{3)}$ | 1 | pH 7.1, 5 mM P-nitro-phenyl glycoside | A | + |
| β-glycosidase | (Asp. aculeatus)$^{4)}$ | 15 | pH 5.0, 0.5% salicin | A | + |
| Gluco amylase | (almond)$^{5)}$ | 10 | pH 5.0, 0.5% salicin | A | — |
|  | (Rhizopus niveus) | 2 | pH 5.5, 0.5% starch | A | — |
| exo-β-1,3-glucanase |  | 15 | pH 6.0, 0.1% laminarin | B | — |
| avicelase | (Asp. aculeatus)$^{4)}$ | 2000 | pH 5.0, 0.5% avicel | C | — |
| Bacterial saccharifying amylase |  | 4 | pH 5.0, 0.5% starch | C | — |
| Bacterial liquefying amylase |  | 0.4 | pH 5.0, 0.5% starch | C | — |
| β-amylase | (sweet potato)$^{5)}$ | 12.5 | pH 5.0, 0.5% starch | C | — |
| Invertase | (bovine colonic mucosa)1) | 5000 | pH 6.0, 0.1% sucrose | A | — |
| Taka-amylase A$^{9)}$ | (yeast)$^{8)}$ | 100 | pH 5.5, 0.1% sucrose | A | — |
|  |  | 0.5 | pH 5.5, 0.5% starch | 69 |  |
| Carboxymethyl-cellulase | (Asp. aculeatus)$^{4)}$ | 100 | pH 5.0, 0.5% CM cellulose | C | — |
| Isoamylase$^{10)}$ |  | 100 | pH 5.5, 0.5% starch | C | — |

++: ID50 ≤ 1.0 μg
+: ID50 ≥ 1.0 μg
—: no inhibition
*: unit (nmol glucose/min)

(Notes)
1): mucosal acetone powder Sigma (M-2766)
2): Sigma (M-8778)
3): produced by TOYOBO Co., Ltd.
4): a crude enzyme (prepared by University of Osaka Prefecture)
5): Sigma
6): produced by Seikagaku Kogyo Co., Ltd.
7): produced by Daiwa Kasei Co., Ltd.
8): Wako Pure Chemicals Co., Ltd.
9): SANKYO Co., Ltd.
10): Shin Nippon Kagaku Co., Ltd.

Method:

Each enzyme (200 μl) is incubated with Trehalostatin (0.01–50 μg) in 0.05 M acetate (pH 5–6) or phosphate (pH 6–7) buffer solution at 37° C. for 5 minutes. Then 20 μl of the resulting solution is collected and added with a substrate to a final concentration shown in the Table, making the total volume of the solution 100 μl. The mixture is incubated at 37° C. for 10 minutes and then incubated in a boiling water bath for 3 minutes to terminate the reaction.

Determination of activity was made by measuring the increase of the product in the reaction system according to the following methods A–C.

The quantity of Trehalostatin which can effect 50% inhibition of enzyme activity under the above-described conditions was indicated as ID$_{50}$.

(A) The glucose produced was determined by the new blood sugar test devised by Boehringer-Mannheim Ltd.

(B) An amount of glucose produced was determined according to the method shown in D. R. Barras and B. A. Stone, Biochim. Biophys. Acta, 191, 329 (1969).

(C) The increase of an amount of reducing sugar produced was measured according to the method shown in J. A. Thoma et al., The Enzyme, 3rd. ed., Ch. 5, pp. 115–189 (1971).

INDUSTRIAL APPLICABILITY

Trehalostatin of the present invention exhibits an effective inhibitory effect against trehalase in insects, especially in Aldrichina grahami, even at a very low concentration and is thus useful as an insecticide for these insects.

What is claimed is:

1. The substance designated trehalostatin, which has the following biological properties:
   a. an inhibitory effect against the enzyme trehalase;
   b. an inhibitory effect against the enzyme α-glycosidase; and
   c. an inhibitory effect against the enzyme β-glycosidase;

said substance trehalostatin being obtainable from Amycolatopsis trehalostatica which has FERM accession number BP-2784; and wherein the substance trehalostatin has the following physical characteristics:

i) is a white powder soluble in water, but which is either hardly or only slightly soluble in hexane, benzene, diethyl ether and petroleum ether;
ii) has no absorption maxima at 220 nm or above in the ultraviolet and visible light absorption spectrum;
iii) has a positive Rydon-Smith reaction and negative ninhydrin reaction, 3,6-dinitrophthalic acid reaction and Elson-Morgan reaction;
iv) has an $R_f$ value of 0.37 in Merck Kieselgal 60 $F_{254}$ thin-layer chromatography using a 3:1:2 mixture of n-butanol, acetic acid and water as a developing solvent;
v) has an Rt of 11.0 minutes in YMC PA03 (0.7×27 cm) high performance liquid chromatography using 65% v/v acetonitrile in $H_2O$ as a solvent at a flow rate of 1.0 ml/min;
vi) has a molecular weight of 366;
vii) has an $[\alpha]_D$ of +115°; and
viii) has NMR spectral data as follows:

$^1$H-NMR/$D_2O$:
3.3 (ppm), dd, 1 H;
3.5 (ppm), m, 1 H;
3.5 (ppm), t, 1 H;
3.6 (ppm), d, 1 H;
3.6 (ppm), dd, 1 H;
3.7 (ppm), d, 1 H;
3.7 (ppm), dd, 1 H;
3.8 (ppm), ddd, 1 H;
4.1 (ppm), dd, 1 H;
4.2 (ppm), d, 1 H;
4.8 (ppm), ddd, 1 H;
5.2 (ppm), d, 1 H;

$^{13}$C-NMR/$D_2O$:
63.5 (ppm);
64.8 (ppm);
72.4 (ppm);
72.8 (ppm);
74.8 (ppm);
75.8 (ppm);
76.2 (ppm);
83.0 (ppm);
83.2 (ppm);
83.4 (ppm);
85.6 (ppm);
89.9 (ppm);
163.8 (ppm).

2. A process for the preparation of the substance trehalostatin as defined in claim 1, which comprises culturing the actinomycete *Amycolatopsis trehalostatica* which has FERM accession number BP-2784, in an assimilable aqueous nutrient medium at a growth sustaining temperature for said actinomycete and for a sufficient time to produce the substance trehalostatin, and recovering the trehalostatin from said medium.

3. A method of killing insects by inhibiting the enzyme trehalase in vivo, comprising contacting said insects with an effective trehalase inhibiting amount of trehalostatin.

* * * * *